(12) United States Patent
Russo (10) Patent No.: US 10,478,167 B2
(45) Date of Patent: Nov. 19, 2019

(54) MEDICAL ADHESIVE APPLICATOR

(71) Applicant: Rousseau Research, Inc., Palo Alto, CA (US)

(72) Inventor: Joseph D. Russo, Palo Alto, CA (US)

(73) Assignee: Rousseau Research, Inc., Palo Alto, CA (US)

( * ) Notice: Subject to any disclaimer, the term of this patent is extended or adjusted under 35 U.S.C. 154(b) by 22 days.

(21) Appl. No.: 15/944,648

(22) Filed: Apr. 3, 2018

(65) Prior Publication Data

US 2019/0099170 A1 Apr. 4, 2019

Related U.S. Application Data (60) Provisional application No. 62/566,217, filed on Sep. 29, 2017.

(51) Int. Cl.
| | |
|---|---|
| *B43K 5/14* | (2006.01) |
| *A61B 17/00* | (2006.01) |
| *B05D 1/26* | (2006.01) |
| *A61M 35/00* | (2006.01) |
| *A61F 13/40* | (2006.01) |
| *B05C 17/00* | (2006.01) |
| *B05D 1/34* | (2006.01) |

(52) U.S. Cl.
CPC ..... *A61B 17/00491* (2013.01); *A61M 35/003* (2013.01); *A61M 35/006* (2013.01); *B05D 1/26* (2013.01); *A61B 2017/00884* (2013.01); *B05C 17/002* (2013.01); *B05D 1/34* (2013.01)

(58) Field of Classification Search
CPC ... A61B 17/00491; A61B 2017/00884; A61M 35/003; A61M 35/006

USPC .................................................. 401/133, 183
See application file for complete search history.

(56) References Cited

U.S. PATENT DOCUMENTS

| | | | |
|---|---|---|---|
| 5,928,611 A | 7/1999 | Leung | |
| 6,099,807 A | 8/2000 | Leung | |
| 6,352,837 B1 * | 3/2002 | Witcher | A61L 2/28 |
| | | | 435/176 |
| 6,641,219 B2 | 11/2003 | Meshke et al. | |
| 6,641,319 B2 | 11/2003 | May | |
| 6,676,322 B1 | 1/2004 | Leung | |
| 6,743,858 B2 | 6/2004 | Hickey et al. | |

(Continued)

*Primary Examiner* — Jennifer C Chiang
(74) *Attorney, Agent, or Firm* — Sideman & Bancroft LLP; Guy W. Chambers (57) ABSTRACT

Medical adhesive applicators are disclosed which allow medical adhesives to have long storage life and be easily dispensed in a controlled manner. In one embodiment, the applicator has a frangible glass vial with the medical adhesive. The frangible glass vial is held in a plastic enclosure with a dispensing tip. Attached to the plastic enclosure is a squeeze tube capable of imparting air pressure into the enclosure. To dispense medical adhesive quickly and with precision, one simply breaks the frangible glass vial and pushes on the squeeze tube. In another embodiment, the applicator has a proximal chamber containing medical adhesive, a distal chamber for dispensing medical adhesive and one or more rupturable membranes between them. To achieve long shelf life, the applicator chambers and membrane(s) are formed from fluorinated plastic. To dispense medical adhesive, one ruptures the membrane(s) and pushes on the sides of the proximal chamber.

14 Claims, 12 Drawing Sheets

(56) References Cited

U.S. PATENT DOCUMENTS

| | | | |
|---|---|---|---|
| 7,094,250 B2 * | 8/2006 | Stenton | A61B 17/00491 222/546 |
| 7,976,234 B2 * | 7/2011 | May | B29C 45/0046 222/541.4 |
| 8,262,608 B2 * | 9/2012 | Clark | A61B 17/00491 604/91 |
| 8,910,830 B2 * | 12/2014 | May | B05C 17/00553 222/94 |
| 9,089,870 B2 * | 7/2015 | Frazier | B05C 17/00 |
| 9,486,829 B2 * | 11/2016 | Kirk, III | A45D 34/04 |
| 9,827,585 B2 * | 11/2017 | Bintig | B43M 11/06 |
| 2008/0311323 A1 | 12/2008 | Morales | |
| 2013/0004230 A1 | 1/2013 | Kirk, III et al. | |
| 2016/0015373 A1 | 1/2016 | Russo et al. | |

\* cited by examiner

MEDICAL ADHESIVE APPLICATOR

CROSS-REFERENCES TO RELATED APPLICATIONS

This application claims priority to U.S. Provisional Patent Application No. 62/566,217, filed Sep. 29, 2017 and entitled "Medical Adhesive Applicator," the disclosure of which is incorporated by reference in its entirety.

FIELD OF THE INVENTION

The present invention pertains to improved disposable applicators for dispensing fluid compositions, especially medical adhesive compositions.

BACKGROUND OF THE INVENTION

Figure 1:
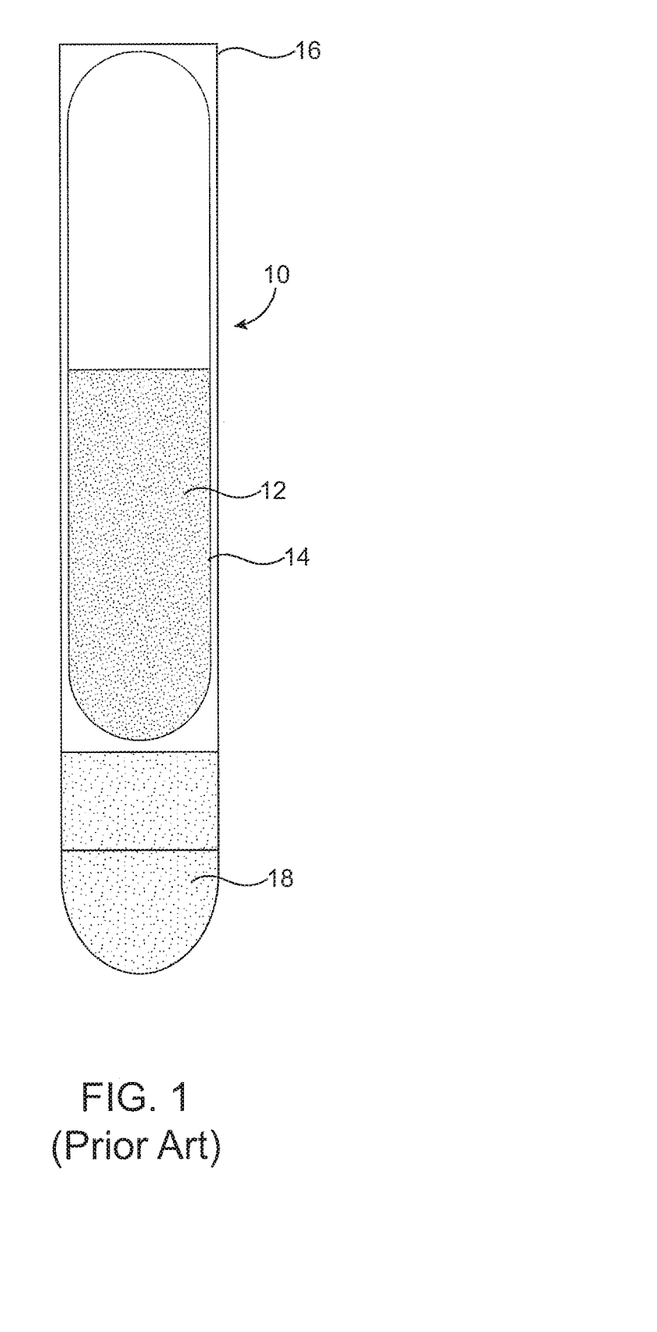
FIG. 1 illustrates a conventional, DERMABOND®-style frangible glass medical adhesive applicator.

In medicine, adhesives are needed for many different purposes, including liquid bandages, wound dressings, skin bonding surgical adhesives, sealants, bioactive release matrixes and implants. Because of the need for sterility in medicine, most medical adhesives are applied from single use adhesive applicators. A popular medical adhesive in a single use applicator is the DERMABOND® medical adhesive developed by Closure Medical Corporation and now sold by Ethicon, a subsidiary of Johnson & Johnson Corporation. As illustrated in FIG. 1 and also described in U.S. Pat. Nos. 5,928,611; 6,099,807 and 6,676,322, an applicator 10 used for the DERMABOND® medical adhesive includes a frangible glass vial 14 held inside a plastic enclosure 16. At the dispensing end of the DERMABOND® plastic enclosure is an applicator tip with a porous plug 18. The porous plug 18 is infused with an accelerator/initiator for accelerating the curing of the DERMABOND® cyanoacrylate adhesive 12. To release the adhesive, one presses on the DERMABOND® plastic enclosure with enough strength to break the frangible glass vial 14. When the frangible glass vial 14 is broken, adhesive slowly flows out of the cracked vial through capillary action and onto the porous plug 18 of the applicator tip. The adhesive can only flow through the porous plug by repetitive squeezing of the plastic enclosure 16. Eventually, the adhesive can be squeezed through the porous plug 18 and applied to the medical use (e.g., sealing a wound). To increase flow rates from squeezing, the DERMABOND® porous tip has been replaced in newer versions with an applicator tip having a porous wafer and a longitudinal hole or lumen. Nonetheless, repetitive squeezing of the plastic enclosure is also required to push adhesive through the porous wafer and longitudinal hole or lumen.

While the DERMABOND® system is in widespread use, it has a number of significant disadvantages. For example, when the DERMABOND® glass vial is crushed, glass shards are created. These glass shards can build up on the porous plug applicator tip. Such a shard build-up can greatly impede the flow of medical adhesive past the build-up. Where the porous plug is replaced by an applicator tip having a longitudinal hole or lumen, the flow of adhesive is increased but so is the possibility of glass shards coming out of the applicator. Obviously, mixing glass shards with medical adhesive is dangerous. Moreover, the flow of adhesive in the DERMABOND® system is difficult to control due to the pressure needed to force the adhesive through the applicator tip. While one can vigorously press on the DERMABOND® plastic enclosure, the DERMABOND® applicator design fails to create a strong, constant force for the adhesive flow. Typically, the adhesive will come out slowly or in spurts— neither of which is desirable in a medical setting where dispensing in a carefully controlled manner is of critical importance. Further, a DERMABOND®-type applicator has a tendency to introduce bubbles into the medical adhesive being dispensed. In adhesives having a water-like viscosity, this is not a big issue because the bubbles tend to break upon emanating from the dispenser tip. However, this is not true for more viscous adhesives, such as the cyanoacrylates used in DERMABOND®, which are activated in the porous plug and, consequently, whose viscosity is already increasing as they are being dispensed.

A form of fluid dispenser is disclosed in May's U.S. Pat. No. 6,641,319 ("May patent"), the disclosure of which is hereby incorporated by reference. Rather than using a glass vial within a plastic enclosure to hold fluid as is done in the DERMABOND® applicator, the May patent creates two chambers in a single plastic enclosure. May's proximal chamber is used to hold unused fluid while May's distal chamber is used to dispense fluid. To separate the two chambers, May places a rupturable membrane between the two chambers in the form of a circular disk with a series of molded radial depressions or weld seams extending from a center point of the disk. When one wants to dispense adhesive from the May applicator, one presses on the outside of May's rupturable membrane until it cracks open and allows fluid to flow from May's proximal chamber to May's distal chamber. With May's membrane ruptured, continued squeezing of May's proximal chamber forces adhesive into May's distal, dispensing chamber and then out of May's applicator altogether.

Even if May's dispenser were used for medical adhesive purposes, May's dispenser would have problems for this application, particularly for cyanoacrylate medical adhesives. Cyanoacrylate monomer compositions, such as those described in Hickey's U.S. Pat. No. 6,743,858, are liquid compositions of monomer that behave like solvents and permeate as well as chemically attack blow molded plastic enclosures made of low-density polyethylene ("LDPE"), mixtures of LDPE and high-density polyethylene ("HDPE"), polypropylene and/or other resins and thus lack the ability to age properly in these containers. The permeation and container wall attack reaction causes the adhesives to polymerize as they age in an applicator made from this group of plastics. By comparison, no permeation occurs in the type of borosilicate glass used in the DERMABOND® frangible glass vials. Due to this permeation and container wall attack in the May dual chamber applicator, cyanoacrylate adhesives typically solidify in several months or earlier in the type of applicator disclosed in May's patent.

Accordingly, there is a need for a medical adhesive applicator where the medical adhesive can be easily dispensed in a controlled manner. There is also a need for a medical adhesive applicator for cyanoacrylate medical adhesives which allows the medical adhesives to not only be easily dispensed but also have a long shelf life.

BRIEF SUMMARY OF THE INVENTION

In one preferred embodiment, the present invention adds a squeeze tube to a conventional type of frangible glass vial and plastic enclosure applicator design, such as that used in the popular DERMABOND® commercial product. The squeeze tube preferably has a neck to seal (e.g., including compression fit, with adhesive, with sealant etc.) around the outside of the plastic enclosure and a bellows section. To allow the squeeze tube of the present invention to easily apply pneumatic pressure to force out adhesive, an aperture is formed at or near the proximal end of the enclosure.

To operate the squeeze tube applicator of the present invention, one begins by pressing the sides of the plastic enclosure in a conventional way to crush the frangible glass vial contained in the plastic enclosure. As the adhesive begins to slowly flow out of the broken glass vial, one then presses on the bellows portion of the squeeze tube to impart pneumatic pressure through the aperture in the enclosure to push adhesive out of the applicator tip. Because of the pneumatic pressure generated by the squeeze tube, the squeeze tube applicator of the present invention can be easily used with porous plug applicator tips which block glass shards from passing out of the applicator. If desired, the squeeze tube applicator of the present invention can also be used with an applicator tip having porous wafer and a longitudinal hole or lumen.

In a second preferred embodiment, a dual chamber applicator is used. As in the May patent, a preferred form of dual chamber applicator has a proximal chamber for holding adhesive, a distal chamber for dispensing adhesive and one or more rupturable membranes between the two chambers in the form of a circular disk(s) with a series of molded radial depressions or weld seams extending from a center point of the disk(s). Unlike May's dual chamber applicator, the plastic used to form the dual chamber applicator of the present invention is fluorinated. This fluorinated plastic allows adhesives in the dual chamber applicator of the present invention, particularly cyanoacrylate adhesives, to have long shelf lives. In the second preferred embodiment, the fluorination preferably takes place when the applicator plastic is formed or when the dual chamber applicator is blow molded. As in the first preferred embodiment, either porous plug applicator tips or applicator tips having a porous wafer with a longitudinal hole or lumen can be used with the dual chamber applicator.

DETAILED DESCRIPTION OF THE INVENTION

Figure 2:
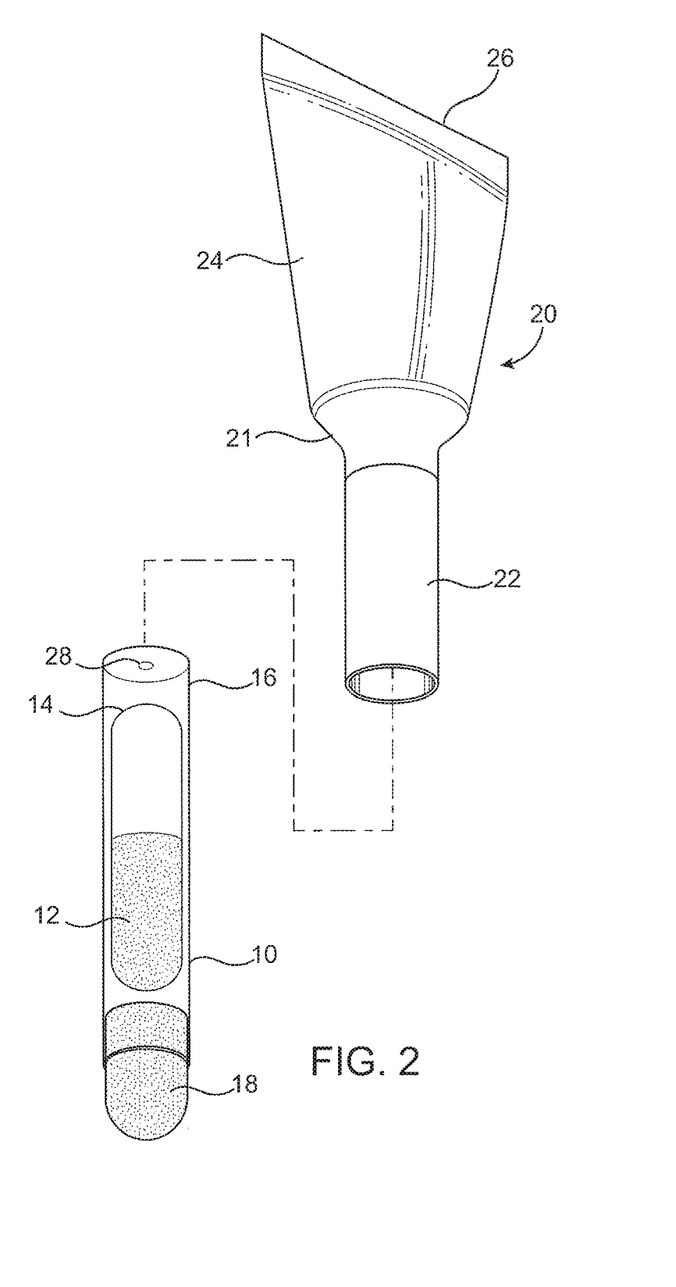
FIG. 2 is an exploded view of a first preferred embodiment where a squeeze tube is added to a modified form of a conventional frangible glass medical adhesive applicator.
Figure 3:
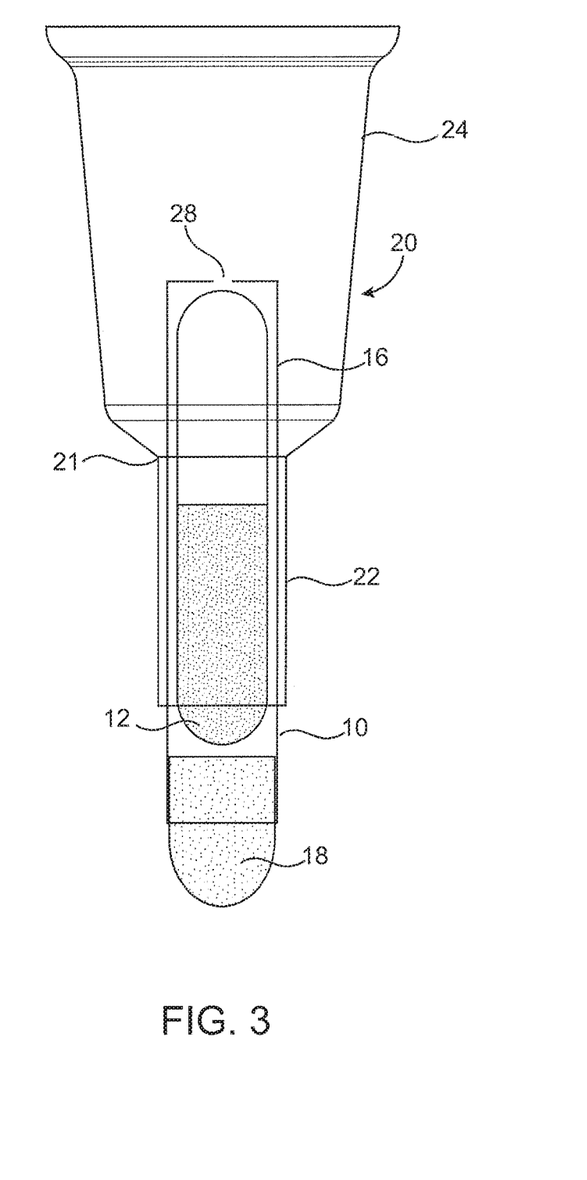
FIG. 3 is an assembled view of the FIG. 2 applicator.

Referring now to FIGS. 2 and 3, a preferred form of squeeze tube applicator 20 of the present invention is shown. In this preferred embodiment, a conventional DERMABOND®-style applicator 10 forms part of the applicator 20 of the present invention. The DERMABOND®-style applicator 10 includes a frangible glass vial 14 holding an adhesive compound 12, a generally cylindrical plastic enclosure 16 holding the frangible glass vial 14 and a porous plug 18. The porous plug 18 is preferably infused with an accelerator and/or initiator for accelerating the curing of adhesive compound 12.

To allow adhesive to be dispensed easily and in a controlled manner, a squeeze tube 21 is added to the DERMABOND®-style applicator 10. The squeeze tube 21 preferably has a proximal bellows portion 24 and a distal neck portion 22. The bellows portion 24 acts like a balloon to store air and allow it to be easily pushed out of the squeeze tube 21. The squeeze tube 21 is preferably made of a flexible plastic. Where the bellows portion 21 is blow molded, it can be sealed by crimping its proximal end 26. The distal neck portion 22 is sized to fit snugly around the outside surface of the plastic enclosure 16 as shown in FIG. 3. This snug, sealing fit can be accomplished by, among other things, a compression fit, with adhesive or with sealant. Where the DERMABOND®-style applicator's plastic enclosure 16 is generally cylindrical in shape, the distal neck portion 22 of the squeeze tube 21 would also be generally cylindrical in shape (but of a slightly larger internal diameter). The objective is to create an air tight seal between the distal neck portion 22 of the squeeze tube 21 and the outside surface of the plastic enclosure 16. To funnel pneumatic pressure from the squeeze tube 21 into the interior of the plastic enclosure 16, an aperture 28 is formed at or about the proximal end of the of the plastic enclosure 16.

As those of skill in the art will recognize, the enclosure 16 of the squeeze tube applicator 20 can have many different shapes, including elliptical, rectangular, square and hexagonal cross-sectional shapes. What is important is that the distal neck portion 22 of the squeeze tube 21 be able to conform to the shape of the enclosure 16 to create an air-tight seal so that the pneumatic pressure created by the bellows portion 24 of the squeeze tube 21 can be focused into the aperture 28 in the enclosure rather than being dissipated. Similarly, while the squeeze tube applicator 20 of the present invention is particularly advantageous for dispensing medical adhesives, such as 2-octyl cyanoacrylates or formulated 2-octyl cyanoacrylates, those of skill in the art will recognize that the squeeze tube applicator 20 of the present invention could also be used for dispensing many other types of fluids.

Figure 4:
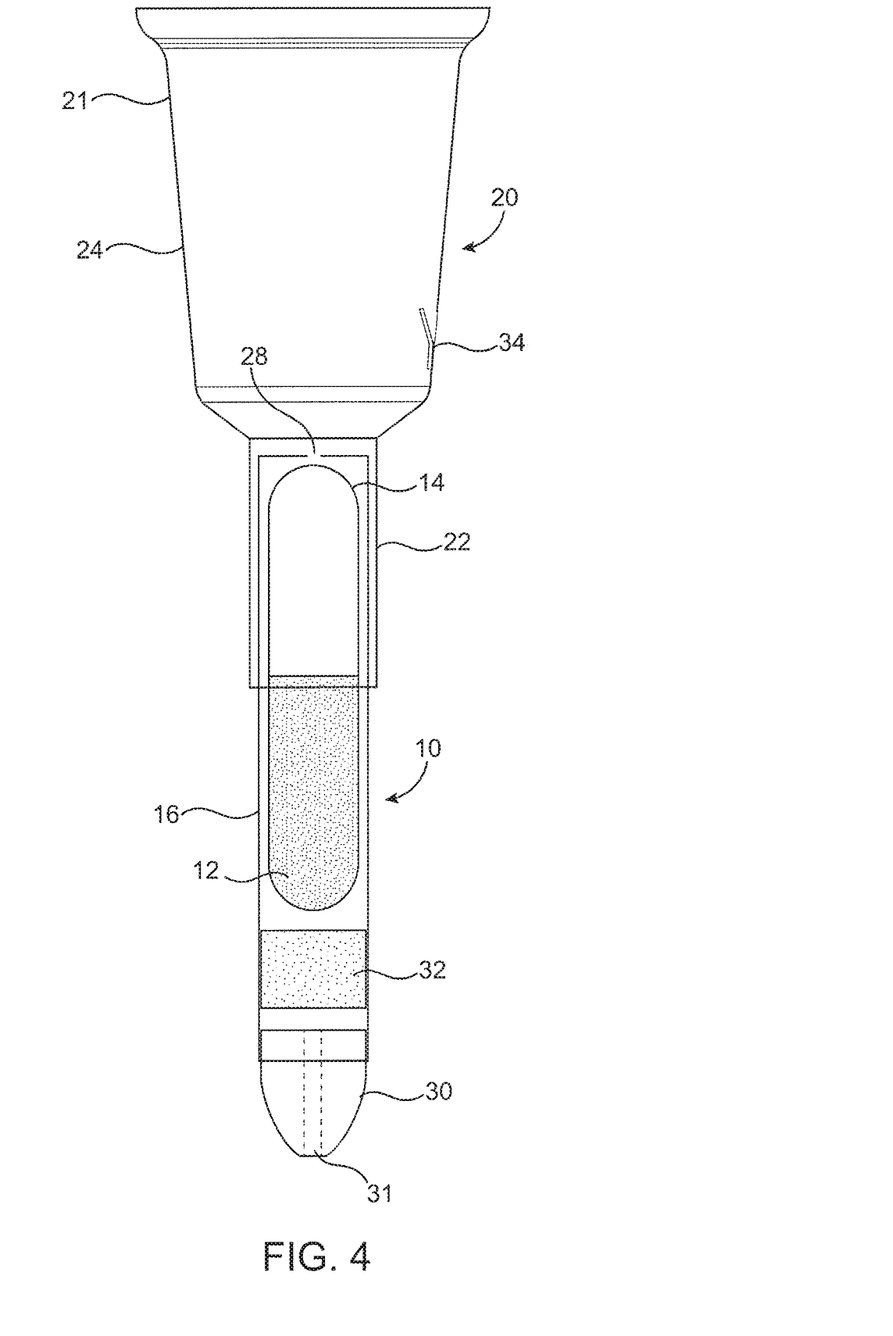
FIG. 4 is an assembled view of a squeeze tube applicator with a longitudinal hole applicator tip and a one-way valve in the bellows portion of the squeeze tube.

FIG. 4 illustrates a modified squeeze tube applicator 20 embodiment. Rather than having a porous plug at the distal end of the enclosure 16, FIG. 4 shows that an applicator tip 30 with a longitudinal hole or lumen 31 placed at the distal end of the enclosure 16 to facilitate adhesive flow. In this embodiment, a porous wafer 32 would preferably be placed above the applicator tip 30 to allow accelerator/initiator to be co-eluted with the adhesive 12 before the adhesive 12 exits through the applicator tip 30 and to help prevent glass shards from the frangible glass vial 14 from passing through the applicator tip 30. FIG. 4 also illustrates that a one-way valve 34 can be placed in the bellows portion 24 of the squeeze tube 21. This one-way valve 34 allows the bellows portion 24 of the squeeze tube 21 to quickly refill with air after it is initially squeezed while preventing air from escaping.

Figure 5:
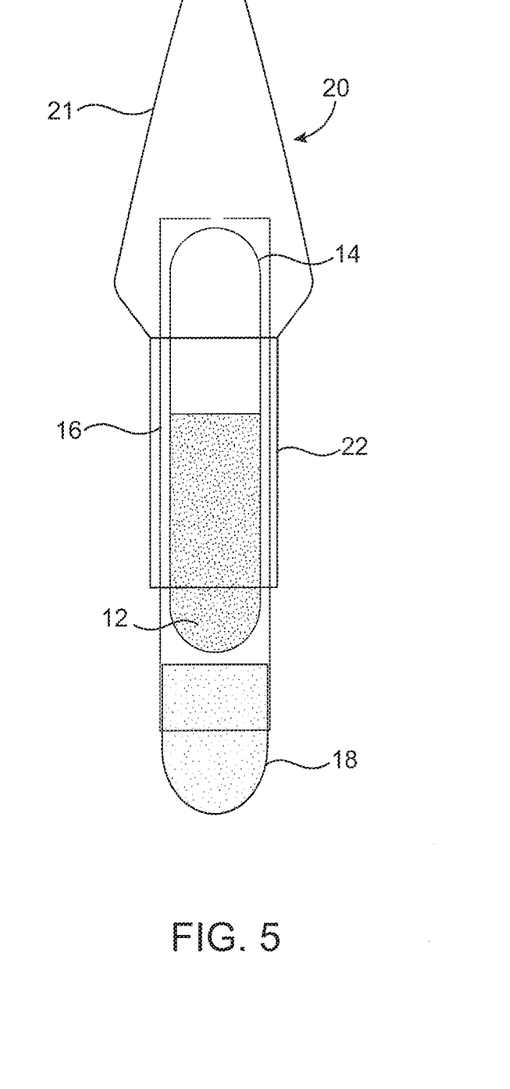
FIG. 5 illustrates the squeeze tube applicator of FIG. 3 prior to use.
Figure 6:
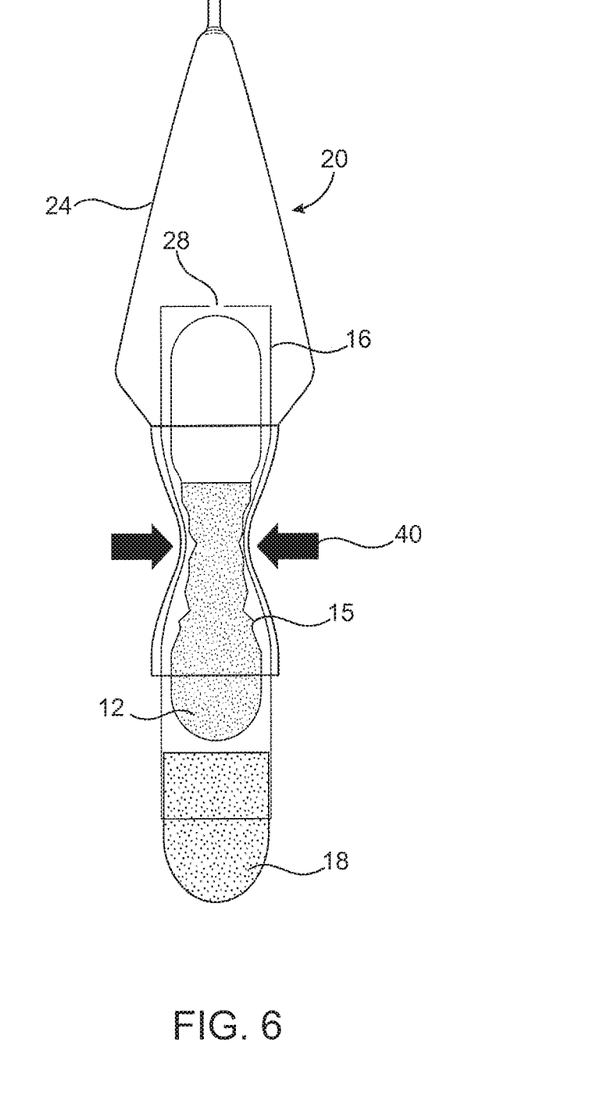
FIG. 6 illustrates pressure applied to the plastic enclosure of the FIG. 3 applicator to break the frangible glass vial.
Figure 7:
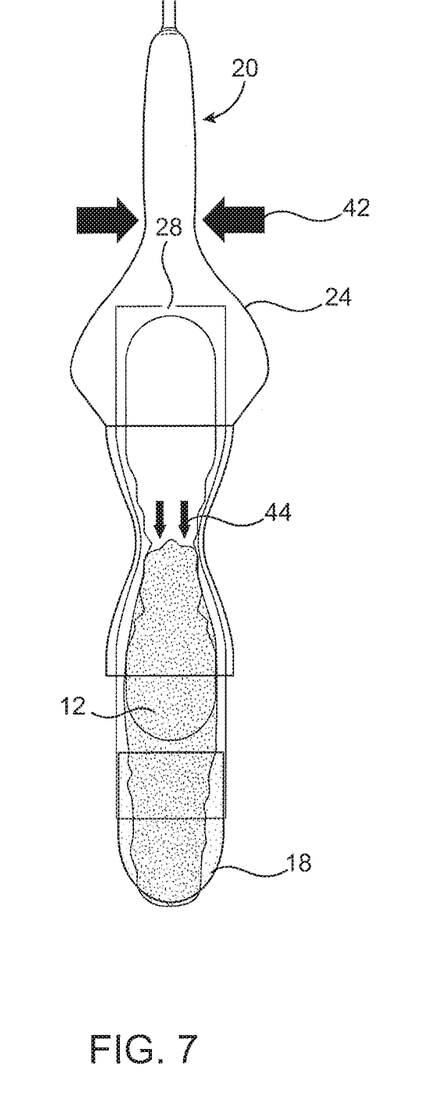
FIG. 7 illustrates how squeezing the squeeze tube of the FIG. 3 applicator creates pneumatic force to drive adhesive out of the broken glass vial and toward the applicator tip.
Figure 8:
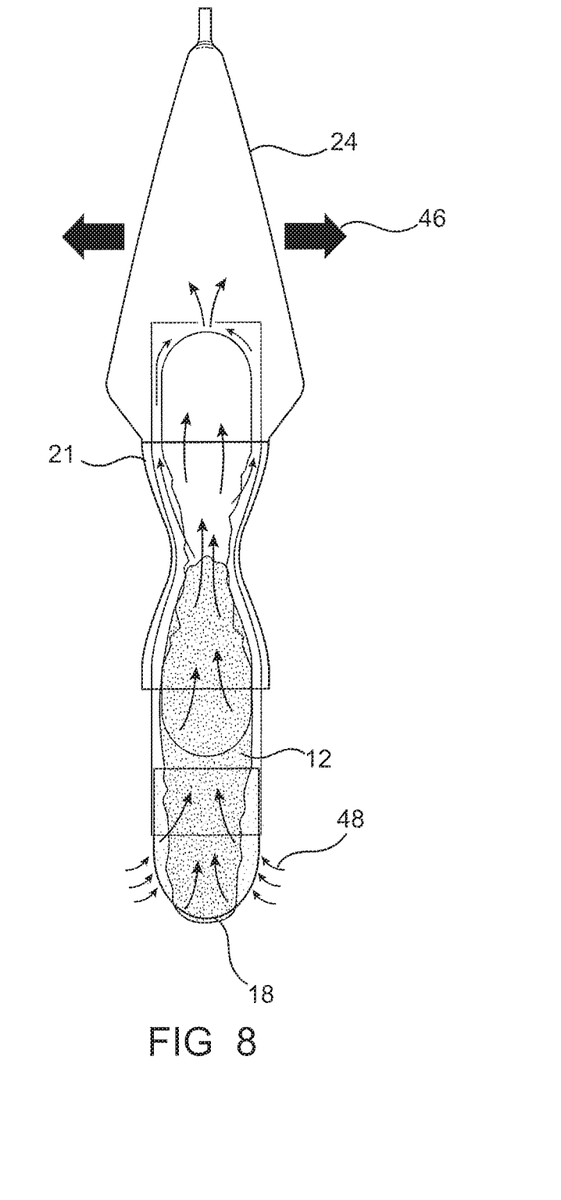
FIG. 8 illustrates how air is pulled back into the FIG. 3 squeeze tube as pressure on the squeeze tube is released.
Figure 9:
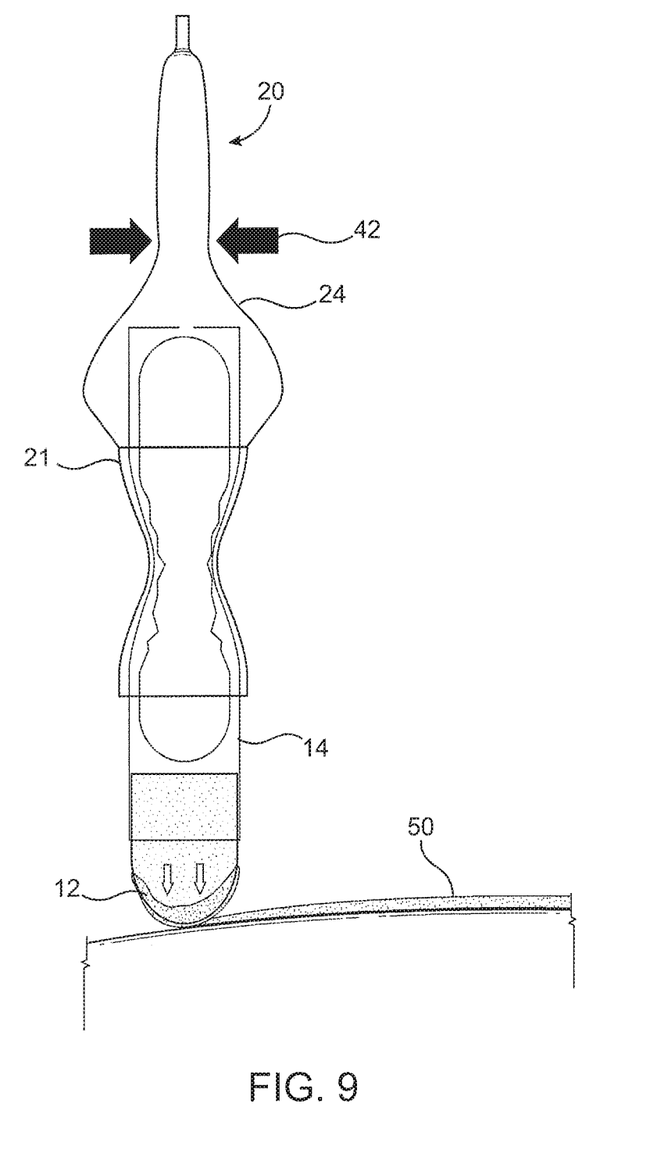
FIG. 9 illustrates how squeezing the squeeze tube of the FIG. 3 applicator a second time forces additional adhesive out of the enclosure.

FIGS. 5-9 illustrate how the squeeze tube applicator 20 of the present invention can be used with very little effort to dispense medical adhesive in a carefully controlled manner. FIG. 5 illustrates the squeeze tube applicator 20 prior to use. The adhesive 12 is stored in a sealed glass vial 14 enclosed within a plastic enclosure 16. At the proximal end of the plastic enclosure 16 is the squeeze tube 21 and at the distal end is a porous plug 18 with accelerator/initiator. As shown in FIG. 6, one releases adhesive 12 from the squeeze tube applicator 20 by first applying simultaneous pressure 40 on the sides of the neck portion 22 of the squeeze tube 21 and enclosure 16 adjacent to the frangible glass vial 14. This pressure 40 is typically provided by the user's fingertips. When sufficient pressure 40 is applied to break the glass vial 14, adhesive 12 flows out of the broken vial and into the plastic enclosure 16. To easily move the adhesive 12 down into the porous plug 18 in a controlled manner, pressure 42 should next be applied to the bellows portion 24 of the squeeze tube 21 as shown in FIG. 7. Again, pressure 42 is typically applied by the user's fingertips. When the bellows portion 24 of the squeeze tube 21 is squeezed in this way, firm air pressure 44 is channeled through aperture 28 and onto the surface of the adhesive 12 in a way that pushes the adhesive 12 into the porous plug 18. Referring now to FIG. 8, when one releases pressure 46 from the bellows portion 24 of the squeeze tube 21, air is drawn 48 into the squeeze tube 21 through the porous plug 18 to refill the bellows portion 24 of the squeeze tube 21 as air flows through the aperture 28. As shown in FIG. 9, with a minimum of additional squeezes 42 of the bellows portion 24 of the squeeze tube 21, once can push out additional adhesive 12 from the plastic enclosure 16 onto the applicator surface 50.

In the prior art DERMABOND® applicator, one had to try to generate pressure by continually pressing on the sides of the plastic enclosure adjacent to the broken glass vial. Most conventional enclosures contain less than approximately 1 ml. volume of air to dispense the liquid. The present invention increases the pneumatic pressure by several times more than conventional applicators. The ingress of air to reload the squeeze tube 21 pressure is enhanced by the volume of liquid displacement in dispensing, giving extremely fine precision control to the user. A 5 ml. applicator, made thusly, dispenses the liquid with great ease, giving the user precision control heretofore unknown in the art. This precision is very valuable to surgeons or medical practitioners. Glass shards which may have blocked flow in a DERMABOND®-style applicator are no longer an impediment to dispensing. Bubbles collapse easily under the higher pressure.

Figure 10:
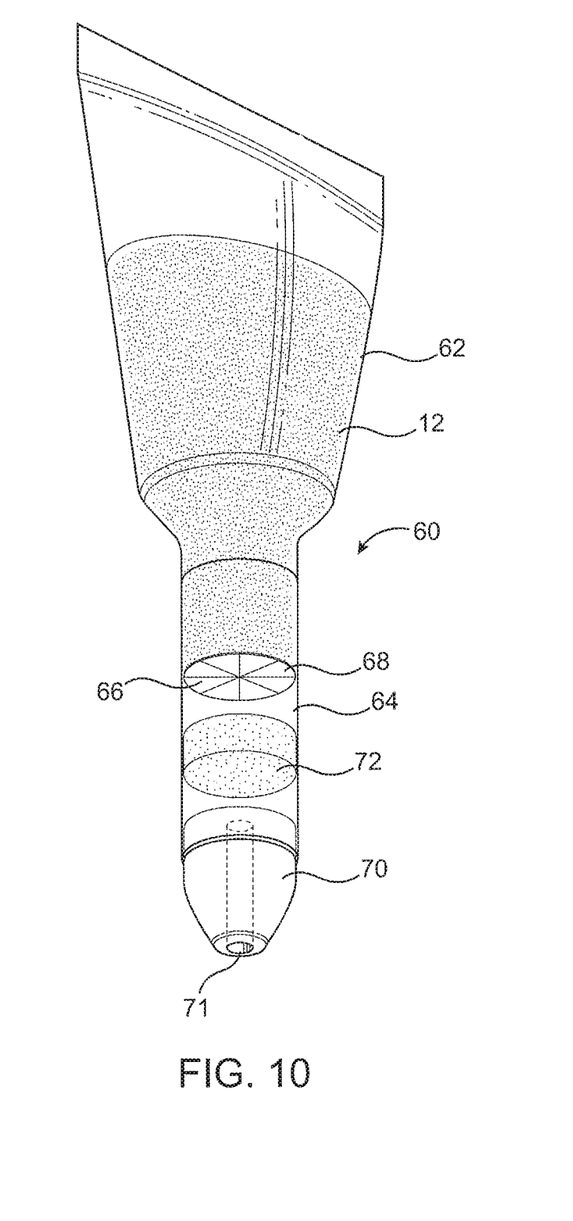
FIG. 10 illustrates a dual chamber adhesive applicator with fluorinated plastic, a rupturable membrane and an applicator tip having a longitudinal hole.
Figure 11:
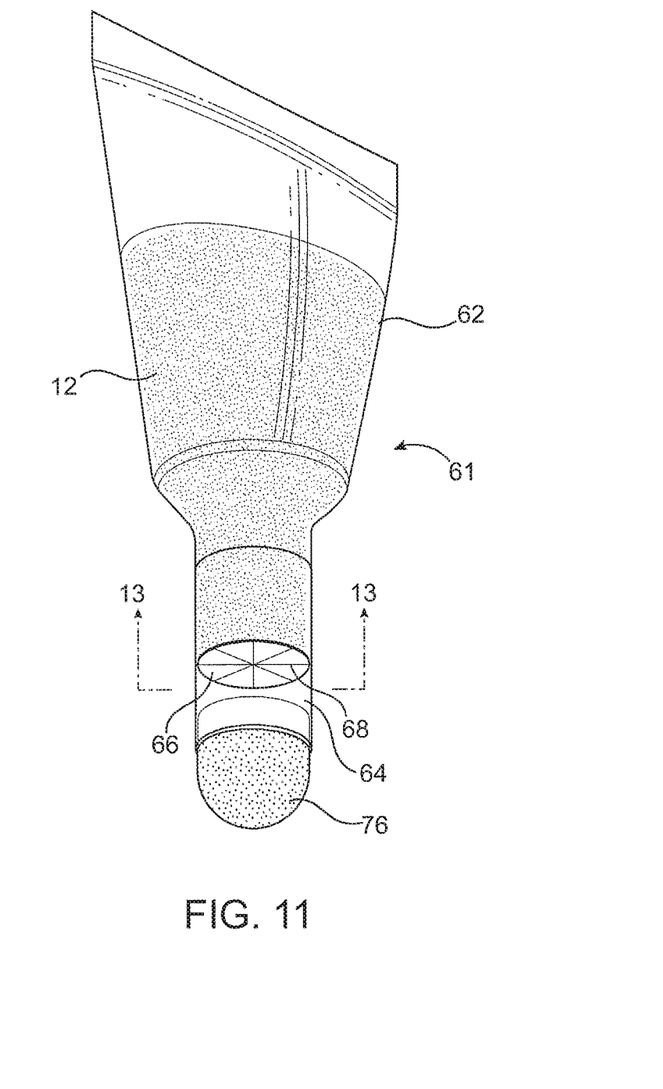
FIG. 11 illustrates a dual chamber adhesive applicator with fluorinated plastic, a rupturable membrane and a porous plug applicator tip.

Referring now to FIGS. 10 and 11, further preferred applicator 60, 61 embodiments are shown. These forms of applicators 60, 61 avoid use of a frangible glass vial and the broken shards of glass associated with such a vial. These alternative applicators 60, 61 are preferably formed from plastic and have two chambers, a proximal chamber 62 to hold adhesive and a distal chamber 64 to dispense adhesive. An applicator tip 70 with a longitudinal hole or lumen 71 can be placed at the end of the distal chamber 64 as shown in FIG. 10 or a porous plug applicator tip 76 can be placed at the end of the distal chamber as shown in FIG. 11. Where the applicator tip 70 with the longitudinal hole or lumen 71 is used, a porous wafer 72 with accelerator/initiator can advantageously be placed between the adhesive 12 and the applicator tip 70 to activate the adhesive during the dispensing process. During manufacture, the two chambers 62, 64 can be formed by a blow molded process. The applicator tip 70, 76 can be inserted by compression fit or by being adhered, heat sealed or solvent welded.

Figure 12:
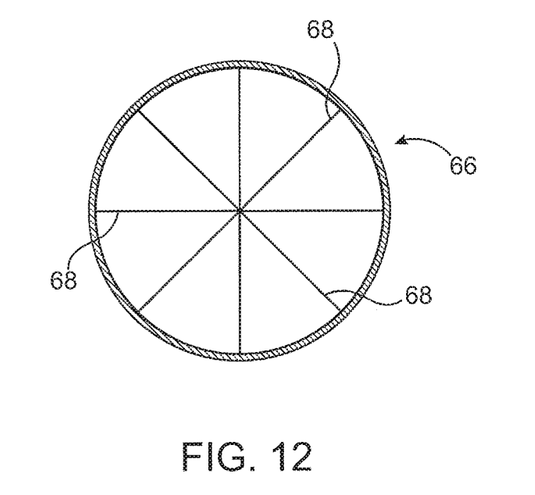
FIG. 12 shows a close-up view of the rupturable membrane of the FIG. 10 applicator prior to the membrane's rupture.
Figure 13:
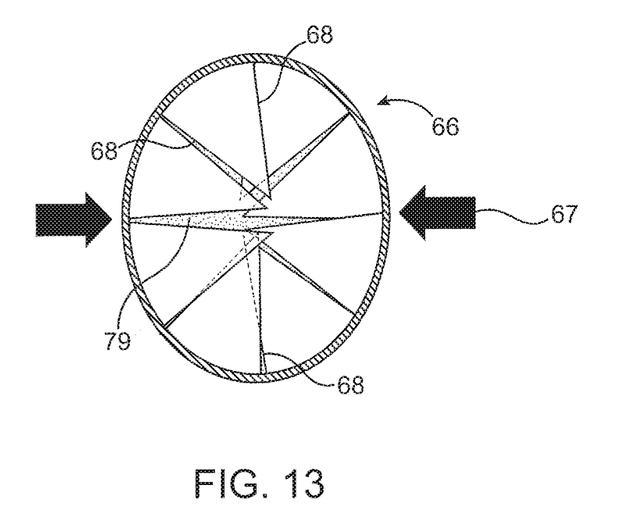
FIG. 13 shows a close-up view of the rupturable membrane of the FIG. 10 aperture after the membrane has been ruptured.

In the FIGS. 10 and 11 embodiments, the two chambers 60, 64 are separated by one or more rupturable membranes 66, preferably in the form of a circular disk scored with a series of molded radial depressions or weld seams 68. Before use, the rupturable membrane(s) 66 acts as an impermeable barrier which holds the adhesive in the proximal chamber 62 and prevents it from moving into the distal chamber 64. A close-up view of a rupturable membrane 66 before use is shown in FIG. 12. Further details about suitable types of rupturable membranes for the present invention are provided in May's U.S. Pat. No. 6,641,219. To allow adhesive to be dispensed from applicators 60, 61, one applies pressure 67 to the sides of the rupturable membrane(s) 66 as shown in FIG. 13. When sufficient pressure is applied, the circular disc 66 ruptures along one or more of the molded radial depressions or weld seams which creates gaps 79 for adhesive 12 to flow from the proximal chamber 62 to the distal chamber 64 and ultimately, after applying further pressure to the sides of the proximal chamber 62, through to the applicator tip 70, 76. By using more than one rupturable membrane 66, one can create a stronger barrier to protect against detrimental permeation and accidental release of adhesive where one of the rupturable barriers is inadvertently damaged or otherwise compromised.

As compared with the FIGS. 1-9 applicator embodiments, the FIGS. 10-13 applicator embodiments have the advantage of being able to hold more adhesive in a comparably sized applicator. A DERMABOND®-style applicator, such as the one illustrated in FIG. 1, typically carries 0.36 to 0.8 ml. of adhesives, enough to cover small incisions or wounds. The increased volume of the rupturable membrane applicators illustrated in FIGS. 10-13 allows for packaging larger volumes of liquid adhesive, thereby making it possible to cover greater area on any substrate. For example, at a higher volume of 2-5 ml. or more, a medical practitioner can cover longer incisions or larger wounds, such as ulcers. Using 2-octyl cyanoacrylate or formulated 2-octyl cyanoacrylate adhesive, an ulcer treatment can be accomplished by barrier sealing ulcers at weekly intervals in place of the more repetitive, expensive daily protocols presently in use.

Where the applicators 60, 61 illustrated in FIGS. 10-13 are formed from the types of plastics that are commonly used for such applicators, such as low-density polyethylene ("LDPE"), mixtures of LDPE and high-density polyethylene ("HDPE"), polypropylene and/or similar resins, problems can develop if those applicators are filled with cyanoacrylate monomer adhesives, such as 2-octyl cyanoacrylate. Cyanoacrylate monomer adhesives, such as those described in Hickey's U.S. Pat. No. 6,743,858, are liquid compositions of monomer that behave like solvents and permeate as well as chemically attack the plastic applicators. The cyanoacrylate adhesives thus lack the ability to age properly in these applicators. The permeation and container wall attack reaction causes the adhesives to polymerize as they age in such applicators.

To overcome this aging problem, the plastic applicators 60, 61 illustrated in FIGS. 10-13 are fluorinated. Fluorinating plastics renders them resistant to permeation by replacing hydrogen atoms in the plastic container surfaces with larger fluorine atoms, thereby creating a barrier. Companies that commercially fluorinate plastics include Fluoro-Seal Corp., Houston, Tex. and their licensee, Betix, Ltd., Bolton, UK. The fluorination preferably takes place when the applicator plastic is formed or when the dual chamber applicator is blow molded. The fluorinating process provides the long shelf life stability desired for applicators holding 2-octyl cyanoacrylate adhesives. Morales U.S. Published Patent Application No. 2008/0311323, which is hereby incorporated by reference, recognizes the value of using fluorinated plastics in connection with cyanoacrylate compounds. Fluorinated plastic also provides an aseptic container and, therefore, highly enhances sterility of the cyanoacrylate adhesive. As a result, the medical adhesive applicator requires less heat or irradiation to attain a FDA sterile approval. Such an aseptic applicator can also take advantage of the sterility method whereby the liquid adhesive can be sterile filtered and filled aseptically. By analogy, it is known by practitioners in the art, for example, that filling frangible glass vials with 2-octyl cyanoacrylate or formulated 2-octyl cyanoacrylate under a nitrogen blanket enhances the stability and sterility of glass vial, i.e., replacing non-sterile oxygen containing ambient air with inert, sterile nitrogen. Such processed filled vials have resulted in greater shelf life and require less radiation to achieve an FDA label as sterile. An inert gas blanket process in like manner applies to the applicators as illustrated in FIGS. 10-13.

EXAMPLES

Example 1

Rate and Consistency of Medical Adhesive Dispensation Using Current DERMABOND® Applicator Experiments were performed to compare the rate and consistency of medical adhesive dispensation using current and legacy DERMABOND® applicators as compared with modified versions of those applicators based upon the principles of the present invention. In the first experiment, a current DERMABOND® DNX12 applicator (Lot LAJ279) filled with 0.70 ml of viscous 2-octyl cyanoacrylate adhesive was used. The current DERMABOND® DNX12 applicator has a longitudinal hole or lumen in its tip and a porous wafer above its tip similar to the embodiment shown in FIG. 4 of the present application. The objective of the experiment was to start flow quickly, preferably on the first squeeze, and dispense at a uniform rate of 0.025 grams per squeeze. TABLE 1 illustrates the measured flows for each squeeze of the DERMABOND® DNX12 plastic enclosure starting when the frangible glass vial was broken by the first squeeze of the plastic enclosure. For all the experiments, the amount of medical adhesive flow was measured by a JDS20 digital milligram scale manufactured by SmartWeigh™ of New York, N.Y.

TABLE 1

| Squeeze | Weight of Dispensed Adhesive (grams) |
| --- | --- |
| 1 | 0 |
| 2 | 0.069 g |
| 3 | 0.025 g |
| 4 | 0.067 g |
| 5 | 0.050 g |
| 6 | 0.022 g |
| 7 | 0.042 g |
| 8 | 0.020 g |
| 9 | 0.025 g |
| 10 | 0.026 g |
| 11 | 0.028 g |
| 12 | 0.026 g (fully dispensed) |

The experimental results show that no medical adhesive was dispensed from the DERMABOND® DNX12 applicator on the first squeeze. On the second squeeze, a much higher amount of medical adhesive (0.069 grams) was dispensed than desired (0.025 grams). The amount of adhesive dispensed during the remaining squeezes continued to be erratic and all had undesirable, problematic bubbles.

Example 2

Rate and Consistency of Medical Adhesive Dispensation Using Modified Version of Current DERMABOND® Applicator For the second experiment, the DERMABOND® DNX12 applicator with viscous 2-octyl cyanoacrylate adhesive was modified in accordance with the principles of the present invention. Similar to the embodiment of the present invention shown in FIG. 4, an aperture was formed at the proximal end of the plastic enclosure and a squeeze tube of the type shown in FIG. 3 (without a one-way valve) was then compression fitted over the plastic enclosure. Again, the objective of the experiment was to start flow quickly, preferably on the first squeeze, and dispense at a uniform rate of 0.025 grams per squeeze. TABLE 2 illustrates the measured flows for each squeeze of the DERMABOND® DNX12 plastic enclosure starting when the frangible glass vial was broken by the first squeeze of the plastic enclosure.

TABLE 2

| Squeeze | Weight of Dispensed Adhesive (grams) |
| --- | --- |
| 1 | 0.046 g |
| 2 | 0.026 g |
| 3 | 0.026 g |
| 4 | 0.026 g |
| 5 | 0.027 g |
| 6 | 0.025 g |
| 7 | 0.024 g |
| 8 | 0.026 g |
| 9 | 0.023 g |
| 10 | 0.023 g |
| 11 | 0.023 g |
| 12 | 0.022 g |
| 13 | 0.035 g |
| 14 | 0.027 g (fully dispensed) |

The experimental results show that, as desired, medical adhesive was dispensed from the modified DERMABOND® DNX12 applicator on the first squeeze, albeit in a somewhat higher amount than desired. On the following squeezes, medical adhesive was dispensed from the modified DERMABOND® DNX12 applicator in a very consistent manner and free of bubbles with very little deviation from the desired 0.025 gram rate. This experiment shows that viscous medical adhesive can be easily and consistently dispensed using a medical adhesive applicator constructed in accordance with the principles of the present invention.

Example 3

Rate and Consistency of Medical Adhesive Dispensation Using a Legacy DERMABOND®-Style Applicator In the third experiment, an older DERMABOND® applicator with viscous 2-octyl cyanoacrylate adhesive as shown in FIG. 1 was recreated (since it is no longer commercially available). This legacy DERMABOND® applicator has a porous plug in its tip as shown in FIG. 1. Because the porous plug tip naturally yields a larger liquid expression than the lumen tip configuration, the objective of the experiment was to start flow quickly, preferably on the first squeeze, and dispense at a uniform rate of 0.033 grams per squeeze. It would be considered to be an acceptable and consistent rate of flow for the porous plug tip if one could control the flow to a range of 0.030 to 0.0360 grams per squeeze. TABLE 3 illustrates the measured flows for each squeeze of the legacy DERMABOND® plastic enclosure starting when the frangible glass vial was broken by the first squeeze.

TABLE 3

| Squeeze | Weight of Dispensed Adhesive (grams) |
|---|---|
| 1 | 0 |
| 2 | 0 |
| 3 | 0 |
| 4 | 0 |
| 5 | 0.035 g |
| 6 | 0.088 g |
| 7 | 0.059 g |
| 8 | 0.031 g |
| 9 | 0.025 g |
| 10 | 0.011 g (fully dispensed) |

The experimental results show that no medical adhesive was dispensed from the DERMABOND® applicator until the fifth squeeze. This may help explain why the legacy DERMABOND® applicator is no longer commercially available. After adhesive began flowing on the fifth squeeze, the amount of adhesive dispensed from squeeze to squeeze was highly erratic.

Example 4

Rate and Consistency of Medical Adhesive Dispensation Using Modified Version of a Legacy DERMABOND®-Style Applicator For the fourth experiment, a recreated legacy DERMABOND® applicator with viscous 2-octyl cyanoacrylate adhesive was modified in accordance with the principles of the present invention. Similar to the embodiment of the present invention shown in FIG. 4, an aperture was formed at the proximal end of the plastic enclosure and a squeeze tube of the type shown in FIG. 3 (without a one-way valve) was then compression fitted over the plastic enclosure. Because a porous plug tip was used, the objective of the experiment was again to start flow quickly, preferably on the first squeeze, and dispense at a uniform rate of 0.033 grams per squeeze. TABLE 4 illustrates the measured flows for each squeeze of the recreated legacy DERMABOND® plastic enclosure starting when the frangible glass vial was broken by the first squeeze of the plastic enclosure.

TABLE 4

| Squeeze | Weight of Dispensed Adhesive (grams) |
|---|---|
| 1 | 0.054 g |
| 2 | 0.031 g |
| 3 | 0.058 g |
| 4 | 0.036 g |
| 5 | 0.031 g |
| 6 | 0.033 g |
| 7 | 0.033 g |
| 8 | 0 (fully dispensed) |

The experimental results show that, with a modification based upon the present invention, medical adhesive was dispensed from the modified legacy DERMABOND® starting with the first squeeze. The amounts dispensed on each squeeze were generally within the acceptable range for a porous plug tip (i.e., 0.030 to 0.036 grams) and were consistent compared with the unmodified legacy DERMABOND® applicator. This experiment shows that a difficult and unreliable DERMABOND® medical adhesive applicator can be made reliable and relatively easy to use if it is modified in accordance with the principles of the present invention.

In the foregoing specification, the invention has been described with reference to specific preferred embodiments and methods. It will, however, be evident to those of skill in the art that various modifications and changes may be made without departing from the broader spirit and scope of the invention as set forth in the appended claims. For example, those of skill in the art will readily appreciate that a variety of materials may be used in making the applicators and applicator tips of the present invention and that those applicators and applicator tips may be made in a variety of dimensions. Moreover, while the focus of the specification has been on medical adhesives, those of skill in the art will recognize that other fluids can be advantageously used in the applicators of the present invention, including other medicaments, cosmetics, cleansing agents, surgical scrubs, paints, other adhesives, sealants, and the like. The specification and drawings are, accordingly, to be regarded in an illustrative, rather than restrictive sense, the invention being limited only by the appended claims.

What is claimed is:

1. A fluid applicator comprising:
   a fluid containing frangible vial inside a plastic enclosure, wherein said enclosure has an aperture at or near its proximal end;
   a squeeze tube sealed to the proximal end of said enclosure to generate air pressure through said aperture; and,
   a dispensing tip at the distal end of said enclosure.

2. The fluid applicator of claim 1 wherein said fluid is a medical adhesive or sealant.

3. The fluid applicator of claim 2 wherein said medical adhesive is 2-octyl cyanoacrylate or formulated 2-octyl cyanoacrylate.

4. The fluid applicator of claim 1 wherein said frangible vial is a frangible glass vial.

5. The fluid applicator of claim 2 wherein said dispensing tip is a porous plug with an accelerator and/or initiator for said medical adhesive.

6. The fluid applicator of claim 2 wherein said dispensing tip has a longitudinal hole or lumen.

7. The fluid applicator of claim 6 further comprising a porous wafer with an accelerator and/or initiator between said frangible vial and said dispensing tip.

8. The fluid applicator of claim 1 further comprising a one-way air valve on said squeeze tube.

9. A method for dispensing medical adhesive comprising:
selecting a fluid applicator having a fluid containing frangible vial inside a plastic enclosure with an aperture at or near the enclosure's proximal end, a squeeze tube sealed to the proximal end of said enclosure and a dispensing tip at the distal end of said enclosure;
squeezing said plastic enclosure to rupture said frangible vial and thereby release fluid from said frangible vial into said plastic enclosure;
squeezing said squeeze tube to force air through said aperture and drive fluid through said dispensing tip.

10. The method of claim 9 wherein said fluid is medical adhesive or sealant.

11. The method of claim 10 wherein said medical adhesive is 2-octyl cyanoacrylate or formulated 2-octyl cyanoacrylate.

12. The method of claim 9 wherein said frangible vial is a frangible glass vial.

13. The method of claim 10 wherein said dispensing tip is a porous plug with accelerator and/or initiator for said medical adhesive.

14. The method of claim 10 wherein said dispensing tip has a longitudinal hole or lumen.

* * * * *